(12) United States Patent
Vassiliades, Jr. et al.

(10) Patent No.: US 6,730,021 B2
(45) Date of Patent: May 4, 2004

(54) TISSUE SPREADER WITH FORCE MEASUREMENT, FORCE INDICATION OR FORCE LIMITATION

(75) Inventors: Thomas A. Vassiliades, Jr., Gulf Breeze, FL (US); Jim Deacon, Goleta, CA (US)

(73) Assignee: Computer Motion, Inc., Sunnyvale, CA (US)

( * ) Notice: Subject to any disclaimer, the term of this patent is extended or adjusted under 35 U.S.C. 154(b) by 188 days.

(21) Appl. No.: 10/006,905

(22) Filed: Nov. 7, 2001

(65) Prior Publication Data
US 2003/0088157 A1 May 8, 2003

(51) Int. Cl.⁷ ................................................ A61B 1/32
(52) U.S. Cl. ....................................... 600/202; 600/215
(58) Field of Search ................................. 600/201, 202, 600/215

(56) References Cited

U.S. PATENT DOCUMENTS

| 3,888,117 | A | * | 6/1975 | Lewis |
| 5,201,325 | A | | 4/1993 | McEwen et al. |
| 5,271,384 | A | | 12/1993 | McEwen et al. |
| 5,704,900 | A | | 1/1998 | Dobrovolny et al. |
| 5,769,781 | A | * | 6/1998 | Chappuis .................... 600/202 |
| 5,888,190 | A | | 3/1999 | Meyer et al. |
| 6,036,641 | A | | 3/2000 | Taylor et al. |
| 6,102,854 | A | | 8/2000 | Cartier et al. |
| 6,113,534 | A | | 9/2000 | Koros et al. |
| 6,290,644 | B1 | | 9/2001 | Green, II et al. |
| 6,306,146 | B1 | | 10/2001 | Dinkler |
| 6,315,718 | B1 | | 11/2001 | Sharratt |
| 6,331,157 | B2 | | 12/2001 | Hancock |
| 6,371,906 | B1 | | 4/2002 | Borst et al. |
| 6,478,734 | B1 | * | 11/2002 | Taylor et al. ................ 600/217 |
| 2002/0014567 | A1 | | 2/2002 | King et al. |
| 2002/0045888 | A1 | | 4/2002 | Ramans et al. |
| 2002/0099268 | A1 | * | 7/2002 | Paul et al. ................... 600/201 |

* cited by examiner

Primary Examiner—Cary E. O'Connor
(74) Attorney, Agent, or Firm—Townsend & Townsend & Crew LLP; Mark D. Barrish, Esq.

(57) ABSTRACT

A retractor with devices that allow a surgeon to control the amount of retractor force. The retractor may include a first blade and a second blade. The second blade can be moved by a gear mechanism. A torque measuring device, force measuring device and/or slip clutch may be coupled to the gear mechanism. The torque measuring device may have a readout that displays the amount of torque being applied by the surgeon to the retractor. The readout provides accurate feedback that allows the surgeon to gauge the amount of force being applied to the patient. Likewise the force measuring device may provide a visual indication of the actual force being applied by the retractor onto the patient. The slip clutch may actuate at a threshold torque to prevent an excessive exertion of force on a patient.

25 Claims, 5 Drawing Sheets

TISSUE SPREADER WITH FORCE MEASUREMENT, FORCE INDICATION OR FORCE LIMITATION

BACKGROUND OF THE INVENTION

1. Field of the Invention

The present invention relates to medical retractors.

2. Background Information

Medical retractors are used to retract tissue and bone of a patient. For example, when performing open heart surgery a surgeon will utilize a retractor to pull apart the rib cage of a patient.

FIGS. 1 and 2 show a retractor 1 of the prior art. The retractor 1 includes a pair of blades 2 and 3 attached to corresponding arms 4 and 5, respectively. Arm 4 is coupled to a rack and pinion gear assembly 6 that allows one blade 2 to move relative to the other blade 3. The pinion is connected to a handle 7 that can be rotated by the surgeon to move the blade 2 and retract tissue and bone.

The amount of spreading is typically controlled by the force applied by the surgeon to the retractor handle 7 and may be estimated by the manual "feel" of the retractor's resistance to handle rotation. Excessive retractor forces may crack or bruise bone, strain supporting cartilage and otherwise cause damage to the patient. This damage increases the amount of post-operative pain and recovery time for the patient. It would be desirable to provide a retractor that would allow the surgeon to more accurately control the amount of force applied to a patient.

BRIEF SUMMARY OF THE INVENTION

A retractor that includes a first blade, a second blade and a gear assembly coupled to the second blade. The retractor also has a torque measuring device, force measuring device and/or slip clutch that allows a surgeon to control the application of force by the retractor.

DETAILED DESCRIPTION

Disclosed are different embodiments of a retractor assembly with devices that allow a surgeon to control the amount of retractor force. The retractor may include a first blade and a second blade. The second blade can be moved by a gear mechanism. A torque measuring device, force measuring device and/or slip clutch may be coupled to the gear mechanism. The torque measuring device may have a readout that displays the amount of torque being applied by the surgeon to the retractor. The readout provides accurate feedback that allows the surgeon to gauge the amount of force being applied to the patient. Likewise the force measuring device may provide a visual indication of the actual force being applied by the retractor onto the patient. The slip clutch may actuate at a threshold torque to prevent an excessive exertion of force on a patient.

Figure 1:
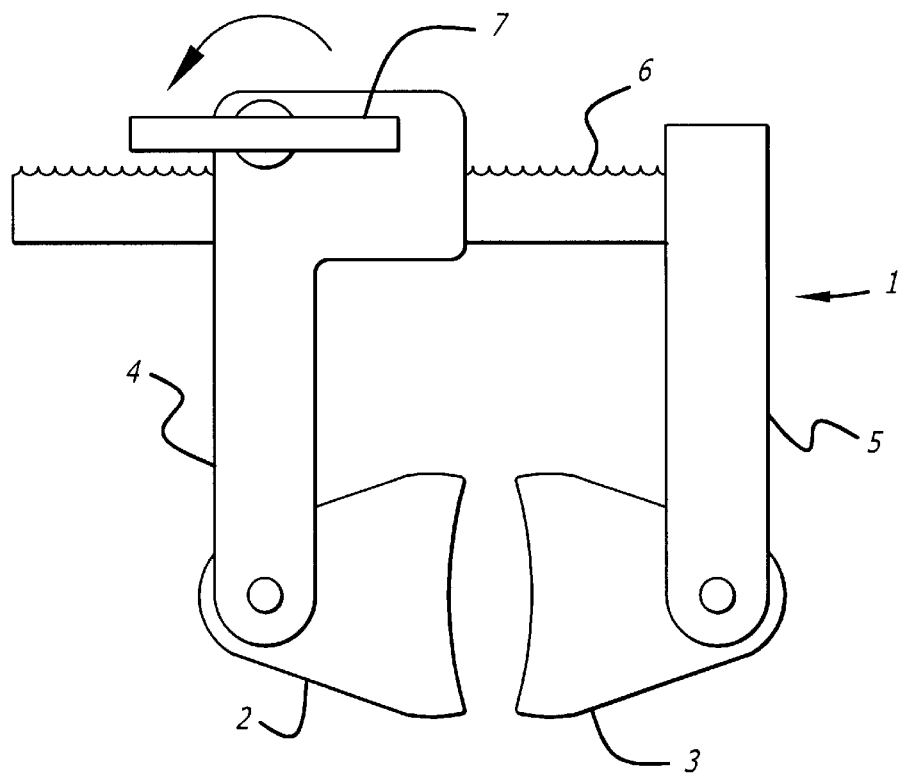
FIG. 1 is a top view of a retractor of the prior art.
Figure 2:
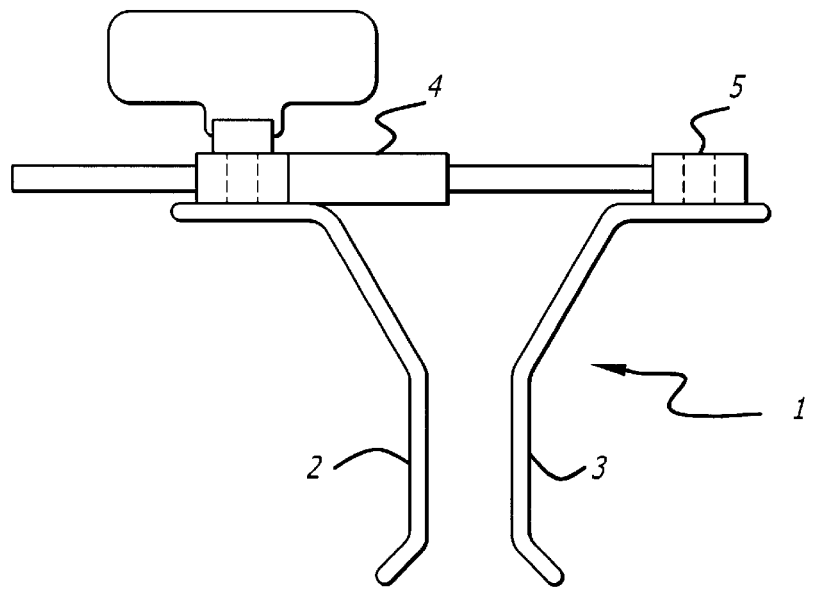
FIG. 2 is a side view of the retractor shown in FIG. 1.
Figure 3:
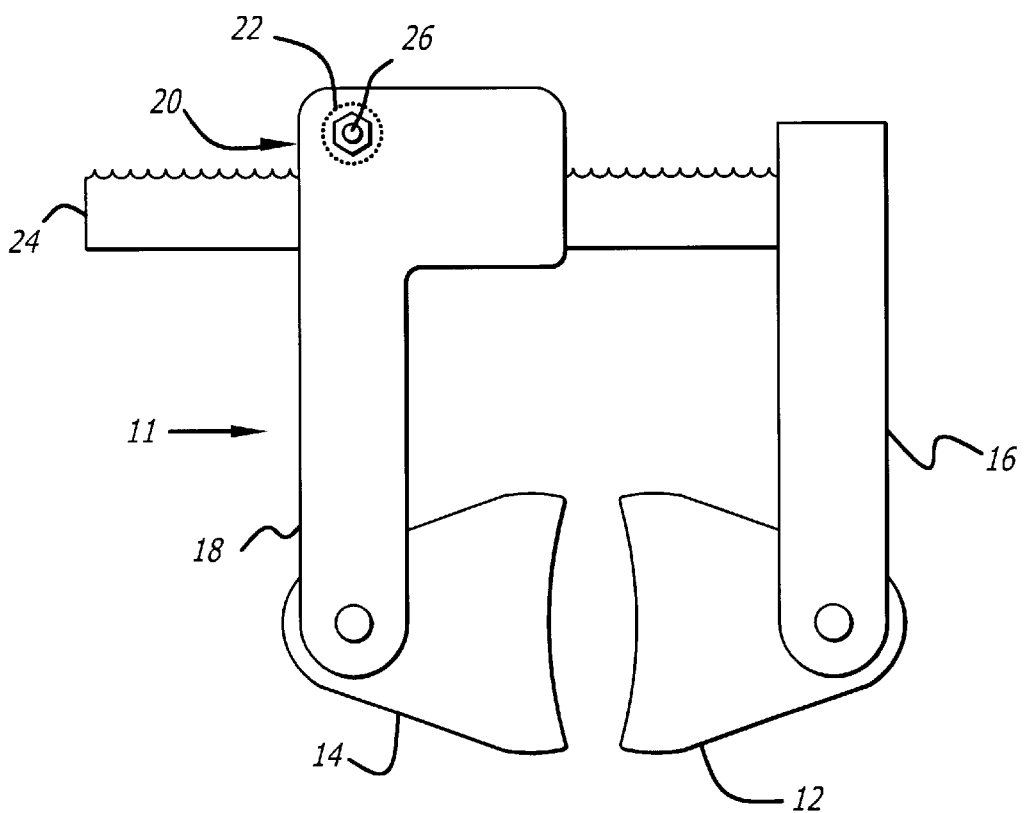
FIG. 3 is a top view of a retractor.
Figure 4:
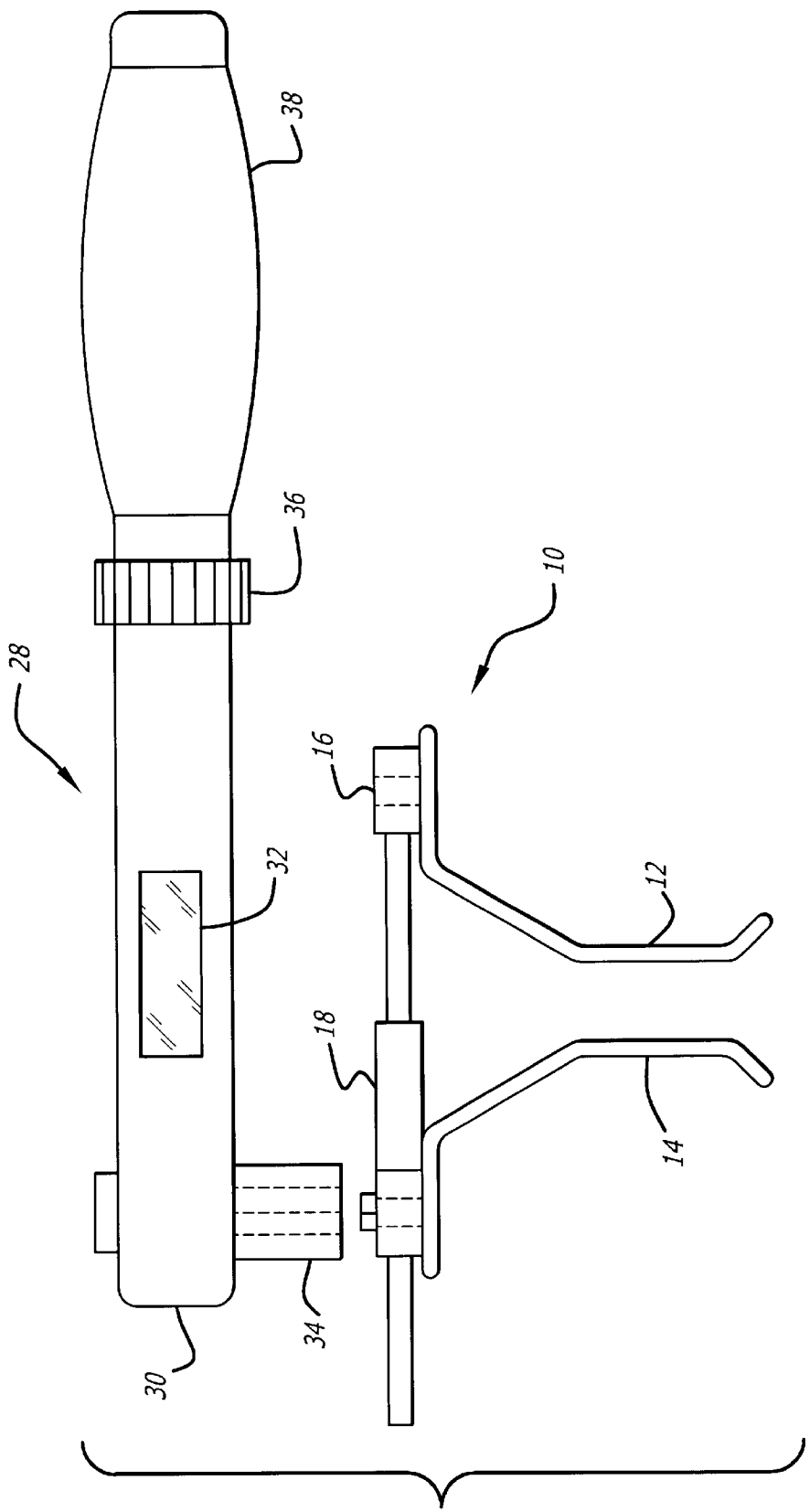
FIG. 4 is a side view of the retractor shown in FIG. 3 with a torque measuring device.

Referring to the drawings more particularly by reference numbers, FIGS. 3 and 4 show an embodiment of a retractor assembly 10. The assembly 10 may include a retractor 11 that has a first blade 12 and a second blade 14. The first blade 12 may be attached to a first arm 16. The second blade 14 may be attached to a second arm 18. The blades 12 and 14 may have a shape that is conducive to retracting tissue and bone of a patient.

The retractor assembly 10 may include a gear assembly 20 that is used to move the second blade 14 relative to the first blade 12. The gear assembly 20 may include a pinion gear 22 that is attached to a second arm 18 and coupled to a rack 24. The rack 24 is attached to the first arm 16. The pinion gear 22 is connected to a hex nut 26.

The retractor assembly 10 may include a torque measuring device 28. The torque measuring device 28 may include a torque wrench 30 with a readout 32 that provides a visual indication of the torque being applied by the wrench 30. The wrench 30 may be coupled to the hex nut 26 by a hex adapter 34. The torque wrench 30 may further have an adjustable slip clutch 36 that allows the user to set the maximum torque that can be applied to the hex nut 26. The slip clutch 36 may be attached to a handle 38.

In operation, a surgeon can insert the blades 12 and 14 into a patient and attach the torque wrench 30 to the hex nut 26. The surgeon can then move the handle 38 to rotate the hex nut 26. Rotation of the hex nut 26 causes the second blade 14 to move and retract tissue, bone, etc. of the patient. The readout 32 provides an indication of the torque being applied so that the surgeon can see when the retractor has reached a maximum torque threshold. This reduces the likelihood that an excessive force will be applied by the blades 12 and 14 to the patient.

Figure 5:
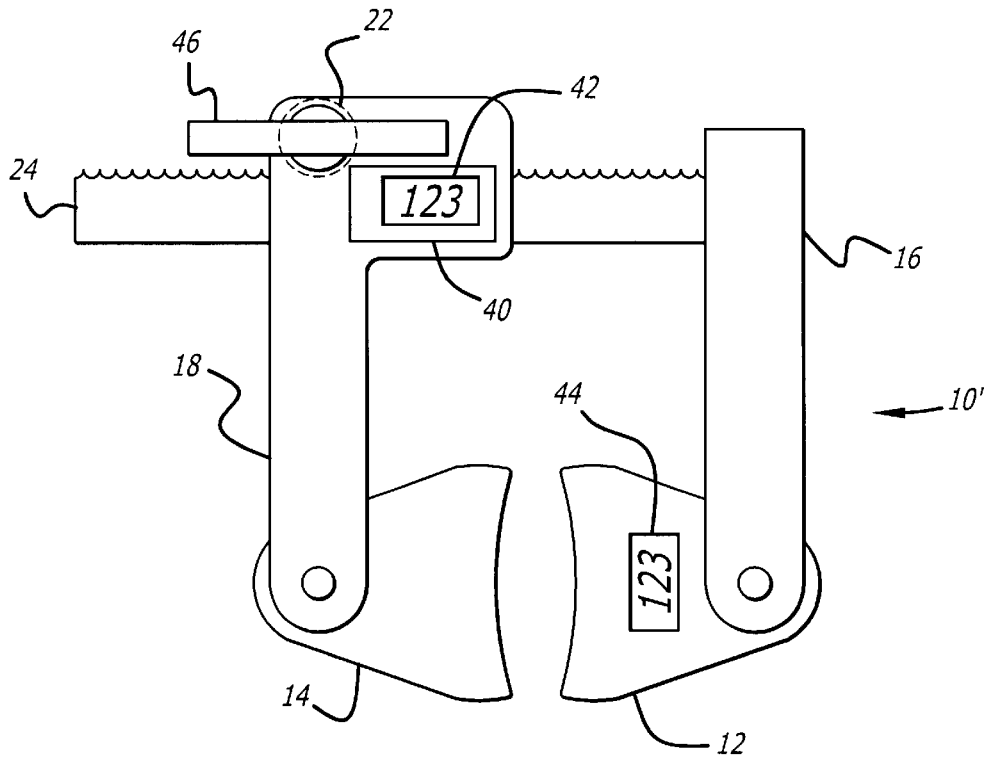
FIG. 5 is a top view of a retractor with a force measuring device.
Figure 6:
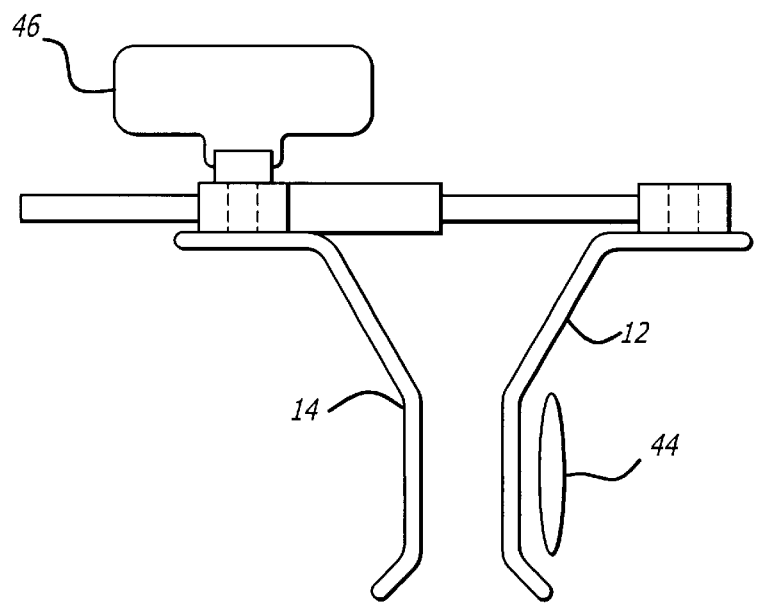
FIG. 6 is a side view of the retractor shown in FIG. 5.

FIGS. 5 and 6 show another embodiment of a retractor assembly 10' that has a force measuring device 40 attached to the second arm 18. The force measuring device 40 may include a readout 42 that provides a visual indication of the force being applied by the blades 12 and 14. The force measuring device 40 may include mechanical or electrical gauges 44 that may be coupled to the pinion gear, arms, and/or directly to a blade. The second blade 16 may be moved by rotating a handle 46 attached to the pinion gear 22.

Figure 7:
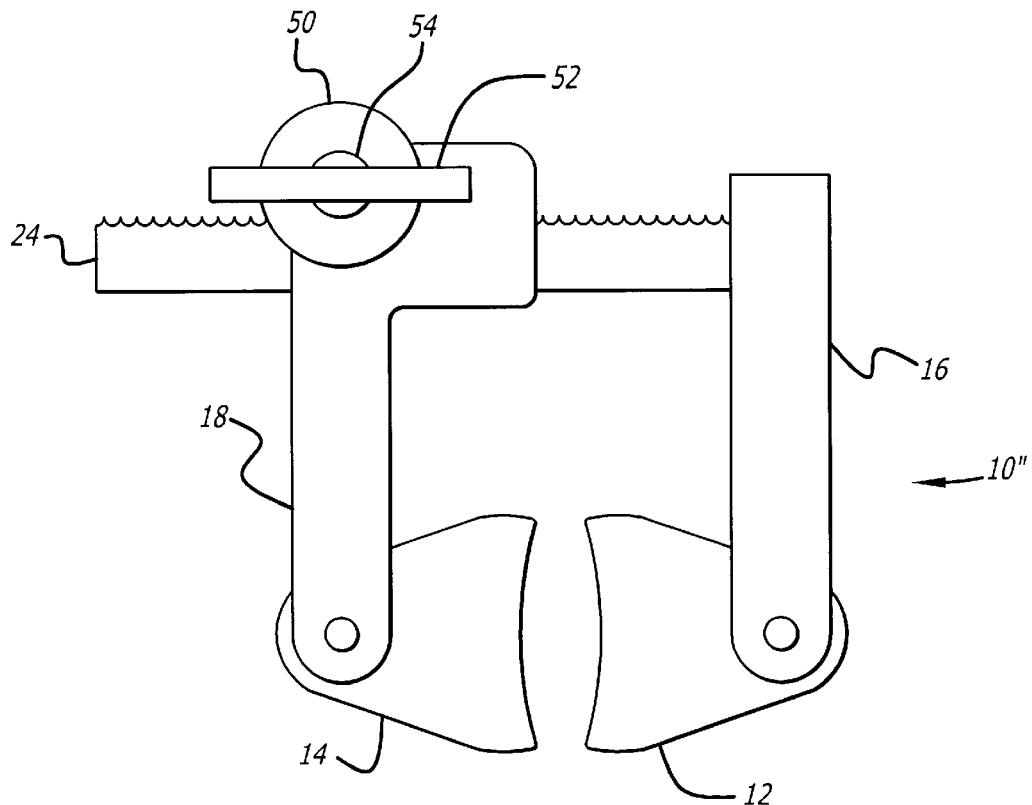
FIG. 7 is a top view of a retractor with a slip clutch.
Figure 8:
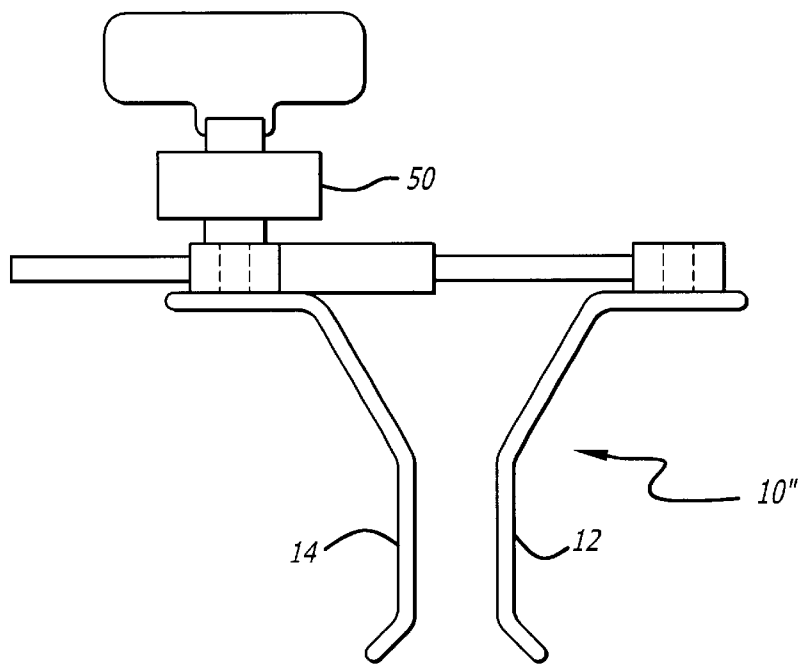
FIG. 8 is a side view of the retractor shown in FIG. 7.

FIGS. 7 and 8 show another embodiment of a retractor assembly 10" that has a slip clutch 50 located between a handle 52 and a gear shaft 54. The slip clutch 50 may prevent further movement and exertion of force by the blades 12 and 14 when the assembly 10" reaches a maximum threshold torque. The slip clutch 50 may be adjustable to allow for variations in the maximum torque threshold. The slip clutch 50 may also be incorporated into the embodiments shown in FIGS. 3–6.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A retractor assembly, comprising: a first blade; a second blade; a gear assembly coupled to said first and second blades; and, a torque measuring device coupled to said gear assembly.

2. The retractor assembly of claim 1, wherein said gear assembly includes a hex nut that is coupled to said torque measuring device.

3. The retractor assembly of claim 1, wherein said gear assembly includes a rack and a pinion gear.

4. The retractor assembly of claim 1, wherein said torque measuring device includes a torque wrench that has a readout.

5. The retractor assembly of claim 1, further comprising a slip clutch coupled to said gear assembly.

6. A retractor assembly, comprising: a first blade; a second blade that can move relative to said first blade; movement means for moving said second blade relative to said first blade; and, torque measuring means for measuring a torque applied to said movement means.

7. The retractor assembly of claim 6, wherein said movement means includes a hex nut that is coupled to said torque measuring means.

8. The retractor assembly of claim 6, wherein said movement means includes a rack and a pinion gear.

9. The retractor assembly of claim 6, wherein said torque measuring means includes a torque wrench that has a readout.

10. The retractor assembly of claim 6, wherein said movement means includes a slip clutch.

11. A method for controlling a retraction of tissue, comprising: inserting a pair of blades into a patient; moving at least one of the blades by exerting a torque; and, measuring the torque.

12. A retractor assembly, comprising: a first blade; a second blade; a gear assembly coupled to said first and second blades; and, a force measuring device coupled to said gear assembly.

13. The retractor assembly of claim 12, wherein said gear assembly includes a hex nut that is coupled to said force measuring device.

14. The retractor assembly of claim 12, wherein said gear assembly includes a rack and a pinion gear.

15. The retractor assembly of claim 12, wherein said force measuring device includes a gauge and a readout.

16. The retractor assembly of claim 12, further comprising a slip clutch coupled to said gear assembly.

17. A retractor assembly, comprising: a first blade; a second blade that can move relative to said first blade; movement means for moving said second blade relative to said first blade; and, force measuring device for measuring a force applied by said second blade.

18. The retractor assembly of claim 17, wherein said movement means includes a hex nut that is coupled to said force measuring device.

19. The retractor assembly of claim 17, wherein said movement means includes a rack and a pinion gear.

20. The retractor assembly of claim 17, wherein said force measuring means includes a gauge and a readout.

21. The retractor assembly of claim 17, wherein said movement means includes a slip clutch.

22. A method for controlling a retraction of tissue, comprising: inserting a pair of blades into a patient; moving at least one of the blades which exerts a force on the patient; and, measuring the force.

23. A retractor assembly, comprising: a first blade; a second blade; a gear assembly coupled to said first and second blades; and, a slip clutch coupled to said gear assembly.

24. The retractor assembly of claim 23, wherein said gear assembly includes a rack and a pinion gear.

25. A retractor assembly, comprising:
a first blade;
a second blade that can move relative to said first blade;
movement means for moving said second blade relative to the first blade, said movement means including a rack and pinion gear; and,
clutch means for limiting the movement of said second blade.

* * * * *